United States Patent [19]
Urrutia

[11] Patent Number: 5,817,068
[45] Date of Patent: Oct. 6, 1998

[54] APPARATUS FOR CONTROLLING FLOW OF BIOLOGICAL/MEDICAL FLUIDS TO AND FROM A PATIENT

[76] Inventor: Hector Urrutia, 2404 W. Augusta Square, McAllen, Tex. 78503

[21] Appl. No.: 784,314

[22] Filed: Jan. 16, 1997

Related U.S. Application Data

[63] Continuation of Ser. No. 394,496, Feb. 27, 1995, abandoned.

[51] Int. Cl.$^6$ ....................................................... A61M 5/00
[52] U.S. Cl. ............................ 604/248; 604/32; 251/207; 251/208; 137/625.41; 137/625.47; 137/605
[58] Field of Search ................................ 604/30, 32, 246, 604/248, 247, 33, 34, 249, 256, 258; 137/625.4, 625.41, 625.42, 625.46, 625.48, 625.14, 625.15, 625.16, 625.44, 625.45, 605, 602, 527, 528, 625.47; 251/207, 208, 209

[56] References Cited

U.S. PATENT DOCUMENTS

| | | | |
|---|---|---|---|
| 926,774 | 7/1909 | Schmidt | 251/207 |
| 1,313,105 | 8/1919 | Moran | 137/625.41 |
| 2,538,215 | 1/1951 | Stack | 604/32 |
| 3,115,896 | 12/1963 | Roberts et al. | 251/207 |
| 3,166,097 | 1/1965 | Hinderer et al. . | |
| 3,477,469 | 11/1969 | Paley . | |
| 3,591,129 | 7/1971 | Hulsey . | |
| 3,654,962 | 4/1972 | Fredd et al. . | |
| 3,722,858 | 3/1973 | Sugimoto et al. . | |
| 3,957,082 | 5/1976 | Fuson et al. | 604/80 |
| 4,146,055 | 3/1979 | Ryder et al. . | |
| 4,165,763 | 8/1979 | Hough | 137/625.41 |
| 4,219,021 | 8/1980 | Fink | 137/625.41 |
| 4,447,236 | 5/1984 | Quinn | 604/248 |
| 4,505,301 | 3/1985 | Yang . | |
| 4,651,775 | 3/1987 | Okada . | |
| 4,667,927 | 5/1987 | Oscarsson . | |
| 4,903,897 | 2/1990 | Hayes . | |
| 4,928,920 | 5/1990 | Feild . | |
| 5,040,566 | 8/1991 | Orlandi | 137/625.41 |
| 5,277,248 | 1/1994 | Breland . | |
| 5,305,790 | 4/1994 | Giacomini . | |

FOREIGN PATENT DOCUMENTS

| | | |
|---|---|---|
| 2099392 | 3/1972 | France . |
| 465222 | 5/1937 | United Kingdom . |

Primary Examiner—Ronald K. Stright, Jr.
Attorney, Agent, or Firm—Oliff & Berridge PLC

[57] ABSTRACT

An apparatus for controlling the flow of fluids between a main conduit and a plurality of secondary conduits includes a valve body having a wall defining a cylindrical bore, the wall having a plurality of ports in respective flow communications with the main conduit and the secondary conduits, and a valve element rotatably disposed within the cylindrical bore of the valve body. The valve element body has internal flow paths with openings flush with a peripheral surface of the valve element body and a channel in flow communication with one of the flow paths, the channel having an opening extending from one of the openings of one of the internal flow paths. In addition, one of the internal flow paths has an enlarged opening to accommodate flow through the channel. The valve element and valve body cooperate to permit fluid flow between the main conduit and a selected one of the secondary conduits by rotating the valve element to align the openings of the channel and the flow paths relative to the ports.

21 Claims, 8 Drawing Sheets

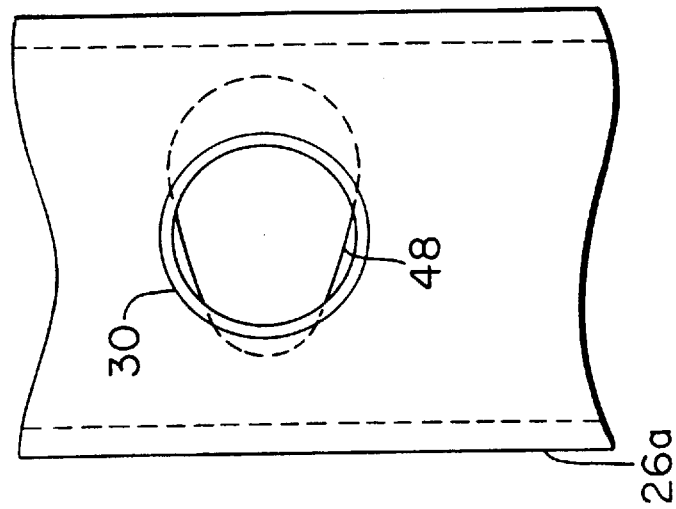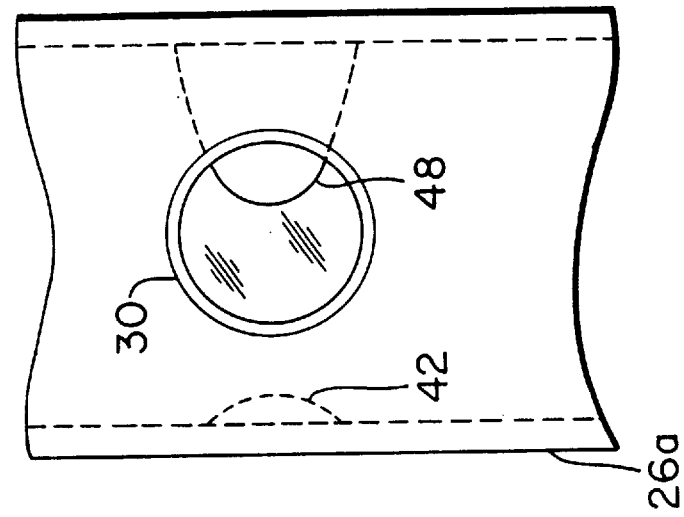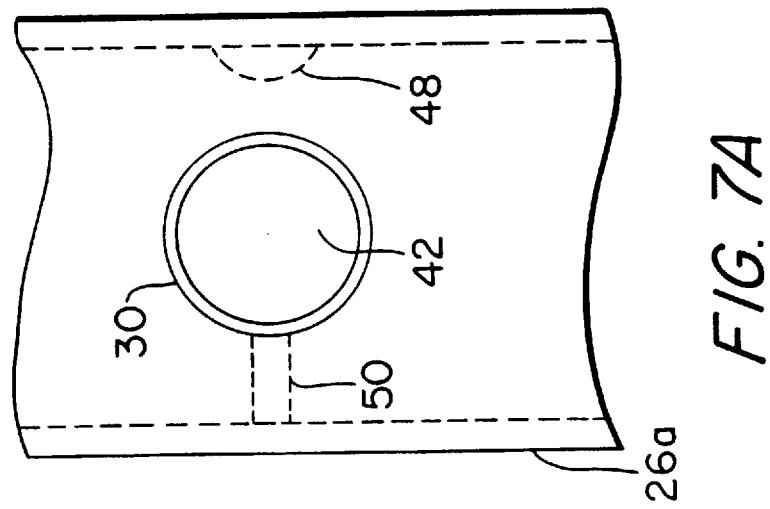

APPARATUS FOR CONTROLLING FLOW OF BIOLOGICAL/MEDICAL FLUIDS TO AND FROM A PATIENT

This is a Continuation of application Ser. No. 08/394,496 filed Feb. 27, 1995 now abandoned.

BACKGROUND OF THE INVENTION

1. Field of the Invention

The present invention relates generally to valves and, more particularly, to a valve for controlling the flow of biological/medical fluids to and from a patient.

2. Discussion of the Related Art

Supplying and withdrawing fluids to and from a patient typically requires invasive procedures, such as intravenous connections via a needle. Thus, when several fluids are transferred to and from a patient, it is advantageous to minimize the number of invasive procedures (i.e., the number of separate intravenous or other connections) since such connections increase risk and cause discomfort to the patient.

In addition, biological fluids withdrawn from a patient may have to be mixed with medical fluids and then returned to the patient. For example, blood may be withdrawn from a patient, mixed with an anticoagulant or other medical fluid, processed, and returned to the patient. As a result, it is advantageous to use a common junction for regulating fluids between plural conduits. Furthermore, the withdrawing, mixing, and injecting of medical/biological fluids generally requires precise control of their flow rates.

There are known manifold valves that allow delivery of several fluids to a patient via one main conduit line attached to the patient. One such manifold valve includes several ports that flow connect the main conduit to one or more secondary conduits. Flow communication between the secondary conduits and the main conduit is controlled by a valve element positioned within a cylindrical valve body that is flow connected to the main and secondary conduits. As shown in FIG. 8, the valve element 100 includes a valve element body 102 rotatably inserted within the valve body (not shown). The valve element body 102 has cylindrical bores that define internal flow paths with openings 104 and 106 flush with a peripheral surface of the valve element body. Alignment of the openings with ports in the valve body permit fluid flow between the main conduit and a selected one of the secondary conduits via the internal flow paths in the valve element.

One of the drawbacks of such a valve is that it is difficult to precisely regulate fluid flow when the valve element is in a position other than fully opened or closed. In other words, it is difficult to incrementally increase or decrease flow rates, given the traditional circular valve opening. Precise regulation of the flow rate is particularly difficult when fluids are being infused under high pressure. As a consequence, conventional valves generally provide an "all-or-nothing" fluid flow, which is disadvantageous, particularly when slower flow rates are desired.

SUMMARY OF THE INVENTION

The present invention is directed to a valve that substantially obviates one or more of the problems due to limitations and disadvantages of the related art.

Additional features and advantages of the invention will be set forth in the description which follows, and in part will be apparent from the description, or may be learned by practice of the invention. The objectives and other advantages of the invention will be realized and attained by the system particularly pointed out in the written description and claims, as well as the appended drawings.

To achieve these and other advantages in accordance with the purpose of the invention, as embodied and broadly described herein, the apparatus of the invention includes a valve body having a wall defining a cylindrical opening, the wall having a plurality of ports in respective flow communication with a main conduit and at least one secondary conduit; and a valve element rotatably disposed within the cylindrical opening of the valve body, the valve element having a peripheral surface contacting the valve body, a first internal flow path having openings flush with the peripheral surface, a second internal flow path intersecting the first flow path and having an opening flush with the peripheral surface, and a channel in flow communication with the first flow path and having an opening flush with the peripheral surface and extending from one of the openings of the first flow path; the valve element and valve body cooperating to permit fluid flow between the main conduit and the secondary conduit by rotating the valve element to align the openings of the channel and the first and second flow paths relative to the plurality of ports, the channel permitting flow through the first flow path when at least a portion of the channel opening is aligned with one of the ports.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

BRIEF DESCRIPTION OF THE DRAWINGS

FIGS. 5A–C, 6A–C, and 7A–C are diagrams showing flow paths through the valve element of FIG. 3.

DESCRIPTION OF THE PREFERRED EMBODIMENT

Figure 1:
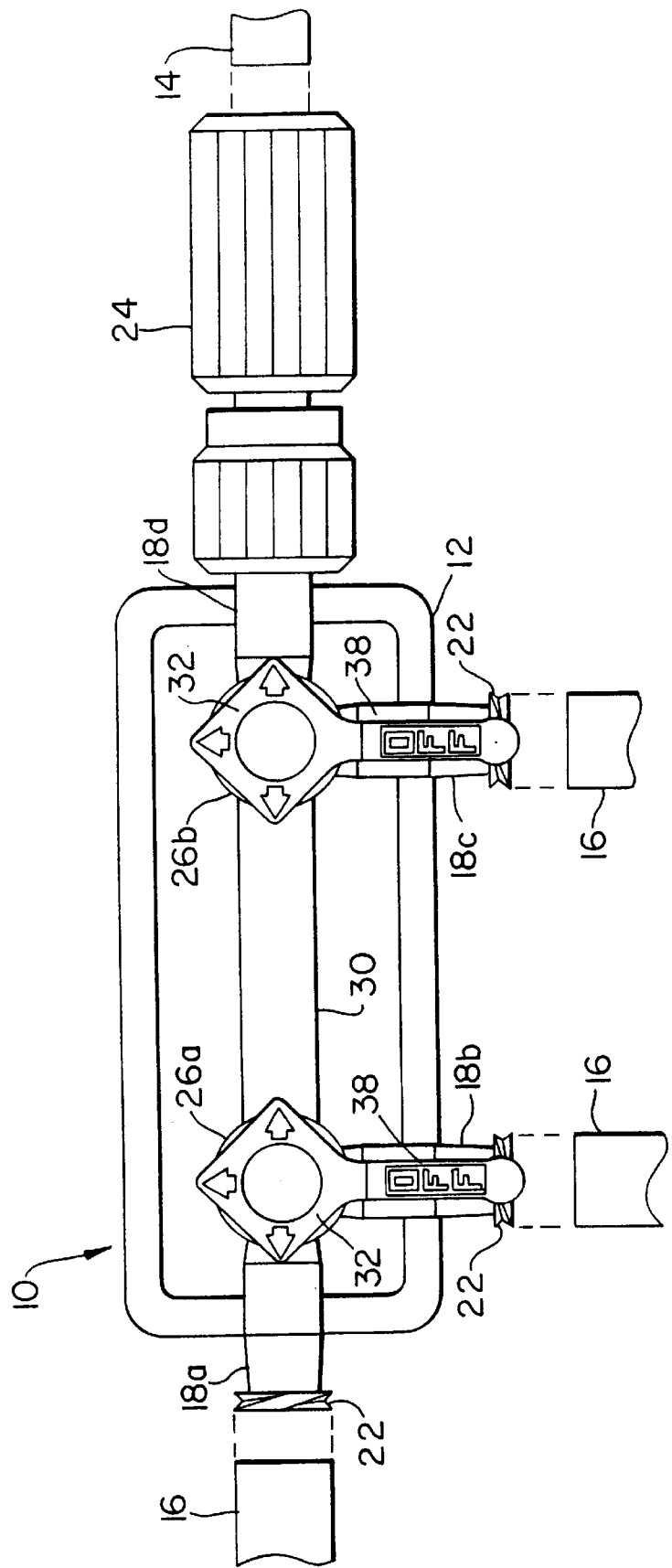
FIG. 1 is a top view of a valve of the present invention.

Reference will now be made in detail to the present preferred embodiment of the invention, an example of which is illustrated in the accompanying drawings. Wherever possible, the same reference characters will be used throughout the drawings to refer to the same or like parts.

Figure 2:
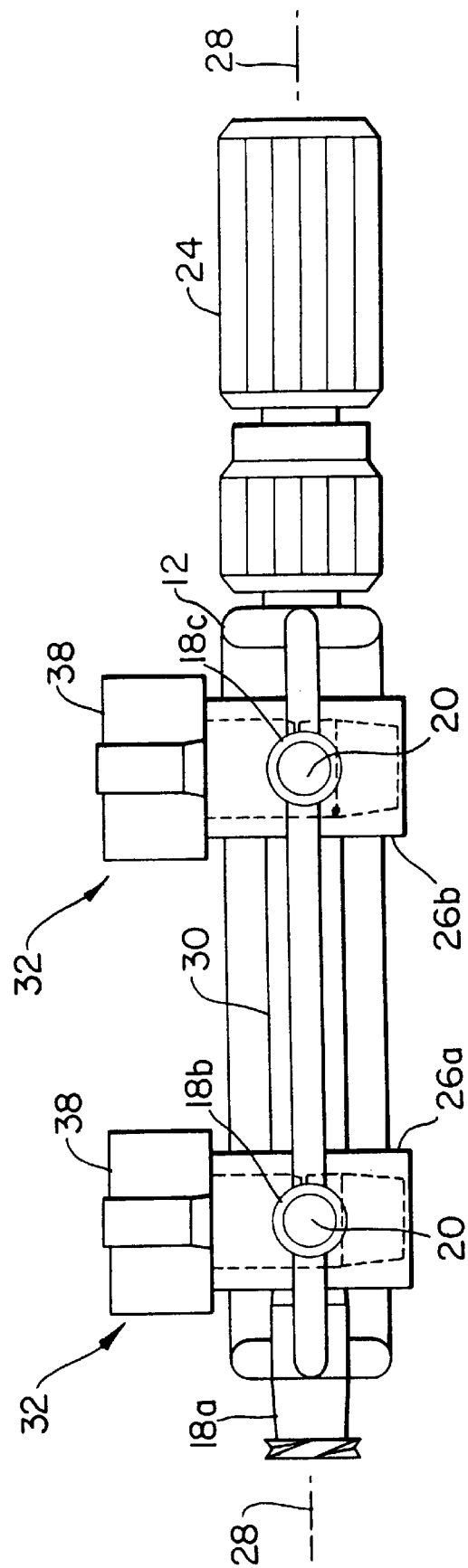
FIG. 2 is a front view of the valve of FIG. 1.

An exemplary embodiment of the valve of the present invention is shown in FIG. 1 and is designated generally by reference numeral 10. As embodied herein and shown in FIGS. 1 and 2, valve 10 includes a manifold 12 for connecting a main conduit 14 (leading to a patient or fluid processing apparatus) in flow communication with one or more secondary conduits 16. The manifold 12 is preferably composed of clear plastic and may be made by injection molding. One type of manifold that may be used is one made by Merit Medical Systems, Inc. of South Jordan, Utah.

The main conduit 14 and secondary conduits 16, which are typically flexible, plastic tubing, are connected to the manifold 12 via ports 18a–d. Each port, which is preferably integral with the manifold, includes a cylindrical passageway 20 (FIG. 2) and a threaded rim 22 for facilitating connection with the conduits. In addition, a threaded connector 24 is provided for coupling port 18d to the main conduit 14.

The manifold 12 also includes valve bodies 26a and 26b. Each valve body includes a cylindrical wall defining a bore extending therethrough in a direction perpendicular to a longitudinal axis 28 of the manifold 12. As shown in FIG. 1, ports 18a and 18b are connected in flow communication with valve body 26a, while ports 18c and 18d are connected in flow communication with valve body 26b. Valve bodies 26a and 26b are also flow connected to each other via an internal passageway 30 formed within the manifold 12. Thus, each valve body is in flow communication with three separate flow paths.

Although two valve bodies and four ports are shown, any number of valve bodies and ports may be included as desired depending on the number of conduits to be attached to the manifold. Also, the valve bodies need not be integral with the manifold, and may be flow connected by a flexible tubing segment instead of internal passageway 30.

Figure 3:
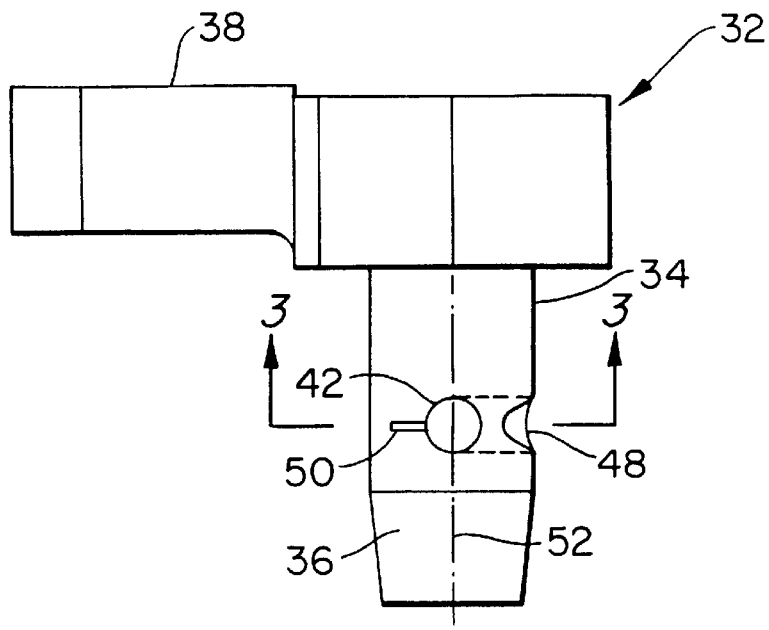
FIG. 3 is a side view of a valve element for the valve of FIG. 1.

Flow between the secondary conduits 16 and the main conduit 14 is controlled by a valve element 32 disposed in each valve body 26a and 26b of the manifold 12. As shown in FIG. 3, valve element 32 has a valve element body 34 with a peripheral surface 36. A handle 38 extends from the valve element body 34 for rotating the valve element 32 within the valve bodies. The valve element is preferably plastic and is sized to snugly fit within the valve body so that fluid does not escape between the cylindrical surfaces of the valve element and the cylindrical wall of the valve body.

Figure 4:
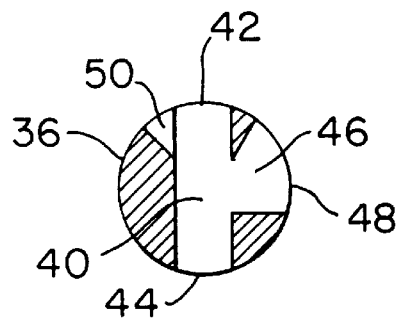
FIG. 4 is a sectional view of the valve element of FIG. 3 taken along the line 3—3.
Figure 8:
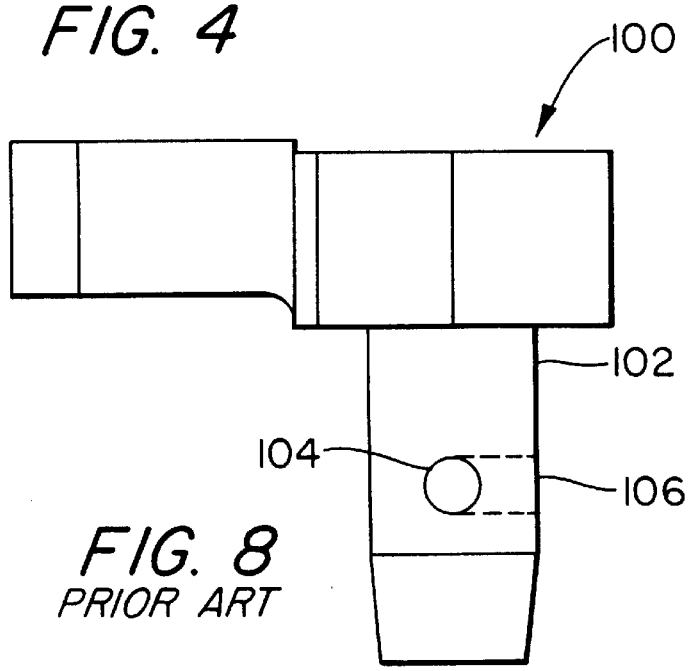
FIG. 8 is a side view of a valve element for a conventional valve.

As shown in FIGS. 3 and 4, a central passageway 40 extends through the valve element body 34 and has two openings 42 and 44 flush with the peripheral surface 36. Passageway 40 is preferably cylindrical and substantially equal in diameter to the diameters of the passageways through ports 18a–d and passageway 30. A second passageway 46 extends through the valve element body 34 in a direction substantially perpendicular to the central passageway 40 and intersects the central passageway 40. The second passageway 46 has an enlarged opening 48 flush with the peripheral surface 36 for accommodating flow through a channel 50. The enlarged opening 48 is larger than opening 44 and may be, for example, substantially elliptical or ovate in shape.

Figure 9:
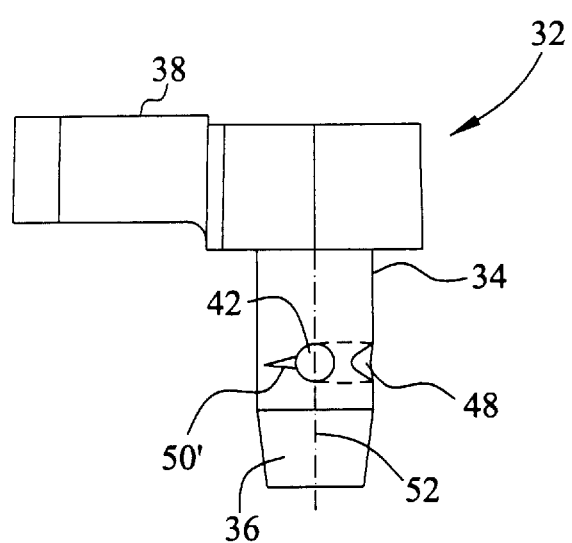
FIGS. 9 and 10 are side views of alternate embodiments of the valve element.
Figure 10:
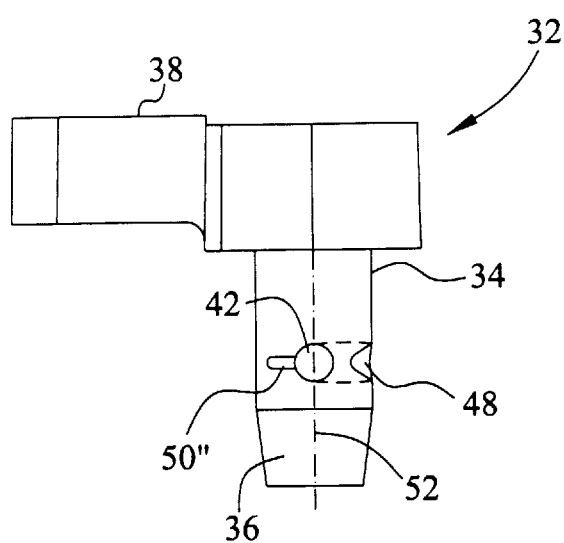

As shown in FIGS. 3 and 4, a narrow channel 50 extends from opening 42 in a direction perpendicular to a central axis 52 of the valve element body 34 and is flow connected to central passageway 40. As shown in FIG. 3, the narrow channel 50 has a substantially rectangular opening flush with the peripheral surface that is smaller in area and in width than opening 42. The channel 50 may be a slit or a bore or any other configuration so long as it provides a lesser flow rate (i.e., a smaller area) than opening 42. Furthermore, the opening of the channel 50 need not be rectangular, but may also be triangular (reference numeral 50' in FIG. 9), elliptical (reference numeral 50" in FIG. 10), and other shapes as well.

Figure 5A:
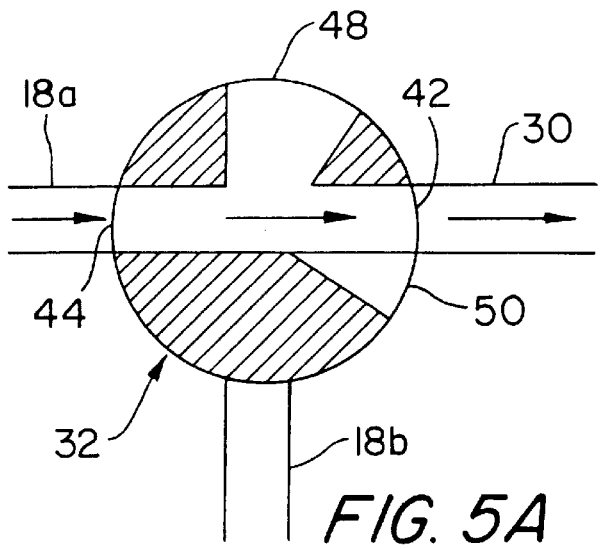
Figure 5B:
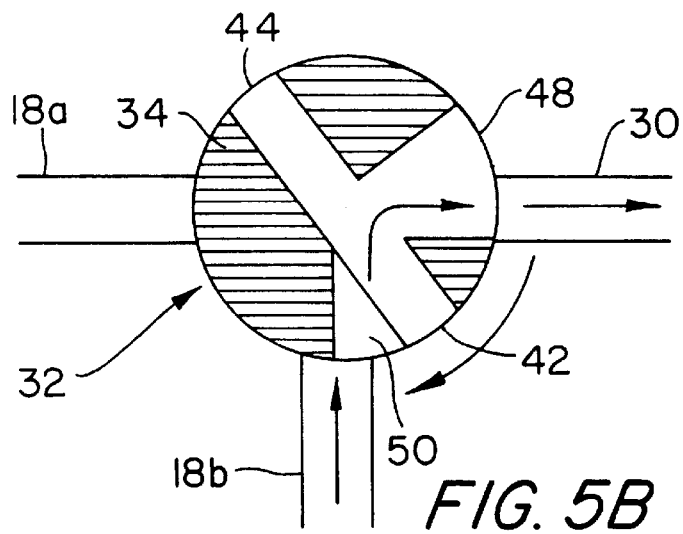
Figure 5C:
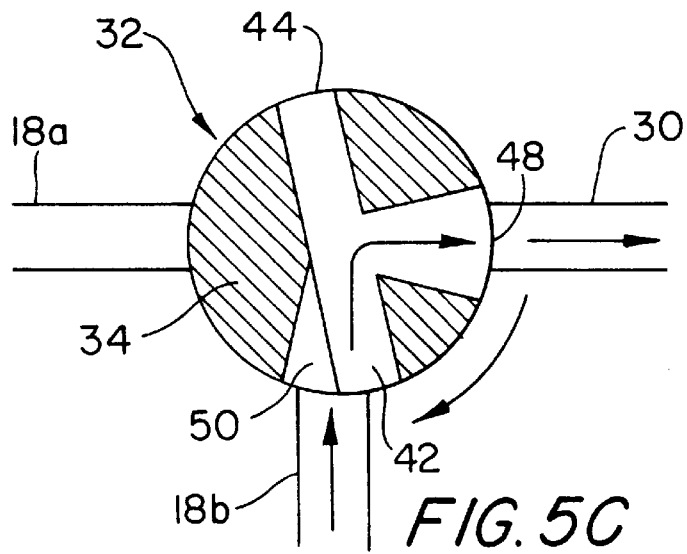

The regulation of fluid flow by the valve element is illustrated in FIGS. 5A–C through 7A–C. FIGS. 5A–C are schematic views of the flow paths through valve element 32, and FIGS. 6A–C and 7A–C are views of the valve element 32 and valve body 26a shown in FIGS. 5A–C as seen through port 18b and internal passageway 30, respectively.

Figure 6C:
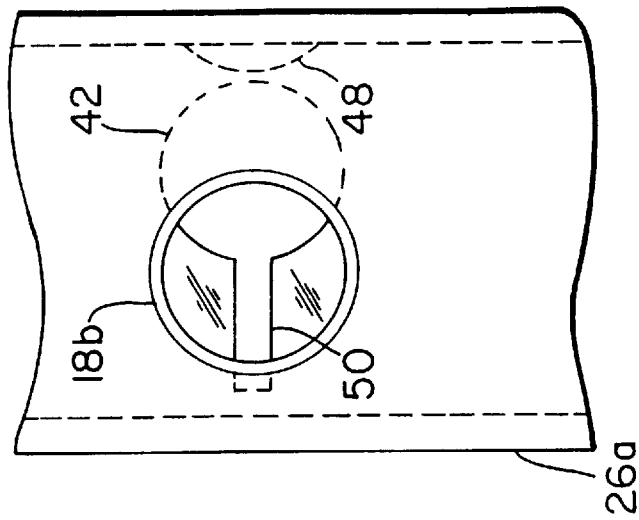
Figure 6B:
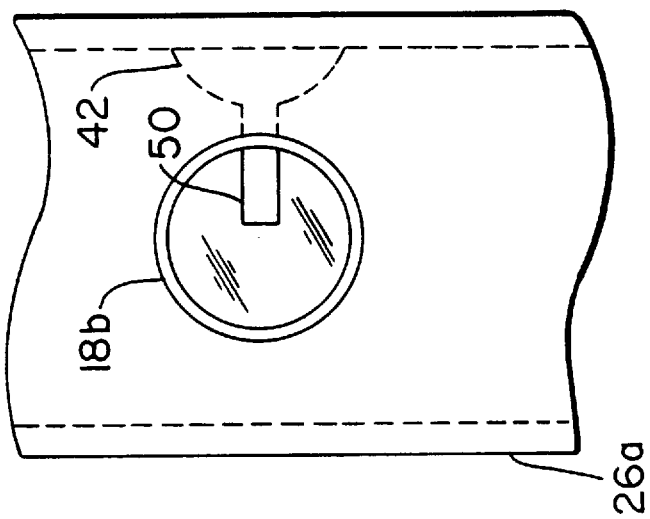
Figure 6A:
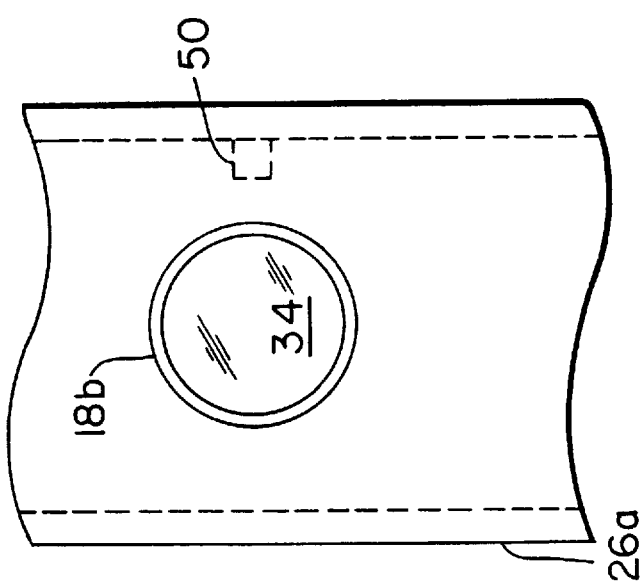

When valve element 32 is in the position shown in FIG. 1, the flow paths through valve element 32 are aligned as shown in FIG. 5A, thus permitting flow between port 18a and passageway 30 and blocking flow between port 18b and passageway 30, as shown in FIGS. 6A and 7A. When valve element 32 is rotated in a clockwise direction to the position shown in FIG. 5B, the valve element body 34 blocks flow to/from port 18a and allows partial flow between port 18b and passageway 30. As shown in FIG. 6B, a portion of channel 50 communicates with port 18b to allow flow proportional to the channel opening area exposed to port 18b. Flow from passageway 40 into passageway 30 via passageway 46 is possible because opening 48 is enlarged to extend around the peripheral surface in the same direction and magnitude as channel 50 extends from opening 42, as shown in FIG. 7B. When the valve element 32 is further rotated in the clockwise direction, as shown in FIGS. 5C, 6C, and 7C, channel 50 and a portion of opening 42 are exposed to port 18b, and a larger portion of opening 48 is exposed to passageway 30, thus allowing a greater rate of flow into passageway 30.

In the above embodiment, each valve element 32 is rotatable ± 90° relative to the valve body. Thus, handle 38 can be rotatable 90° from the position shown in FIG. 1 (over port 18b) to a position over port 18a, or 90° from the position shown in FIG. 1 to a position over passageway 30. Stops may be provided on the manifold or within the valve bodies to prevent further rotation of the valve elements.

Although each valve element 32 shown in the figures includes a channel 50 and an enlarged opening 48, only one valve element may include a channel and an enlarged opening if the flow through the remaining valve(s) is not critical. In addition, the valve element may include a channel in communication with each opening if precise flow regulation through several secondary conduits is desired.

It will be apparent to those skilled in the art that various modifications and variations can be made in the apparatus of the present invention without departing from the scope or spirit of the invention. Thus, it is intended that the present invention cover the modifications and variations of this invention provided they come within the scope of the claims and their equivalents.

What is claimed is:

1. Apparatus for controlling the flow of fluids between a plurality of conduits, comprising:

a manifold including at least one valve body having a wall defining a cylindrical bore, the wall having a plurality of ports in respective flow communications with the plurality of conduits; and a valve element rotatably disposed within the bore of each valve body, each valve element having a peripheral surface contacting the valve body, an internal flow path having first and second openings flush with the peripheral surface, and a channel adjoining and in flow communication with the flow path throughout the length of the channel, the channel having a first end with an opening flush with the peripheral surface and adjoining the first flow path opening and a second end terminating at the intersection with the flow path, the channel opening providing a lesser flow rate into the flow path than the first flow path opening;

each valve element and valve body cooperating to permit fluid flow between selected ones of the conduits by rotating the valve element to align the openings of the channel and the flow path relative to the plurality of ports, the channel and second flow path opening permitting flow through the flow path when at least a portion of the channel opening is aligned with one of the ports and at least a portion of the second flow path opening is aligned with another one of the ports.

2. The apparatus of claim 1, wherein the width of the channel opening in a direction parallel to a longitudinal axis of the valve element is smaller than the width of the first flow path opening from which the channel extends.

3. The apparatus of claim 1, wherein the area of the channel opening is smaller than the area of the first flow path opening from which the channel extends.

4. The apparatus of claim 1, wherein the channel comprises a slit having one of a substantially rectangular, a substantially elliptical, and a substantially triangular cross-section.

5. The apparatus of claim 1, wherein the second flow path opening is larger than the first flow path opening and is arranged on the peripheral surface of the valve element to accommodate flow through the channel.

6. The apparatus of claim 1, wherein the second flow path opening is substantially one of elliptical and ovate in shape.

7. The apparatus of claim 1, wherein the valve element includes a handle for rotating the valve element within the cylindrical bore of the valve body.

8. Apparatus for controlling the flow of fluids between a plurality of conduits, comprising:
   a valve body having a wall defining a cylindrical bore, the wall having a plurality of ports in respective flow communication with the plurality of conduits; and
   a valve element rotatably disposed within the cylindrical bore of the valve body, the valve element having a peripheral surface contacting the valve body, a first internal flow path having openings flush with the peripheral surface, a second internal flow path intersecting the first flow path and having an opening flush with the peripheral surface, and a channel intersecting and in flow communication with the first flow path, the channel having a first end with an opening flush with the peripheral surface and contiguous with one of the openings of the first flow path and a second end terminating at the intersection with the first flow path;
   the valve element and valve body cooperating to permit fluid flow between selected ones of the conduits by rotating the valve element to align the openings of the channel and the first and second flow paths relative to the plurality of ports, the channel and second flow path opening permitting flow through the first and second flow paths when at least a portion of the channel opening is aligned with one of the ports and at least a portion of the second flow path opening is aligned with another one of the ports.

9. The apparatus of claim 8, wherein the channel opening provides a lesser flow rate into the first flow path than the first flow path opening from which the channel extends.

10. The apparatus of claim 8, wherein the width of the channel opening in a direction parallel to a longitudinal axis of the valve element is smaller than the width of the first flow path opening from which the channel extends.

11. The apparatus of claim 8, wherein the area of the channel opening is smaller than the area of the first flow path opening from which the channel extends.

12. The apparatus of claim 8, wherein the channel comprises a slit having one of a substantially rectangular, a substantially elliptical, and a substantially triangular cross-section.

13. The apparatus of claim 8, wherein the second flow path opening is larger than the first flow path opening and is arranged on the peripheral surface of the valve element to accommodate flow through the channel.

14. The apparatus of claim 8, wherein the second flow path opening is substantially one of elliptical and ovate in shape.

15. The apparatus of claim 8, wherein the valve element includes a handle for rotating the valve element within the cylindrical bore of the valve body.

16. Apparatus for controlling the flow of fluids between a plurality of conduits, comprising:
   a valve body having a wall defining a valve seat having a plurality of ports adapted for flow communication with the plurality of conduits; and
   a valve element rotatably disposed within the valve seat, the valve element having a peripheral surface facing the valve seat, an internal flow path having first and second openings flush with the peripheral surface, and a slit defining a channel in flow communication with the flow path, the slit having an opening flush with the peripheral surface and adjoining the first opening of the flow path, the slit sized to provide a lesser flow rate into the flow path than the first flow path opening, the second flow path opening being larger than the first flow path opening and extending around the peripheral surface a distance sufficient to accommodate fluid flow through the slit and the first flow path opening when either the slit or the first flow path opening is aligned with one of the ports.

17. The apparatus of claim 16, wherein the area of the slit opening is smaller than the area of the first flow path opening adjoining the slit.

18. Apparatus for controlling fluid flow between a plurality of conduits, comprising:
   a valve body defining a valve seat having a plurality of ports adapted for flow communication with the plurality of conduits; and
   a valve element movably disposed within the valve seat, the valve element having a peripheral surface facing the valve seat, an internal flow path having first and second openings flush with the peripheral surface, and a channel in flow communication with the flow path, the channel having an opening that is flush with the peripheral surface and is contiguous with the first flow path opening, the area of the channel opening being smaller than that of the first flow path opening to provide a lesser flow rate into the flow path than the first flow path opening, the second flow path opening being positioned on the peripheral surface and being sized to be in flow communication with one of the ports when the channel opening and the first flow path opening are in flow communication with another one of the ports to permit fluid flow through the valve element and the respective ports.

19. The apparatus of claim 18, wherein the channel is contiguous with the flow path throughout the length of the channel.

20. The apparatus of claim 18, wherein the channel has a first end adjacent the peripheral surface and a second end terminating at an intersection with the flow path.

21. The apparatus of claim 18, wherein the channel and first flow path openings, in combination, extend around the peripheral surface for a predetermined distance, the second flow path opening extending around the peripheral surface a distance no less than the predetermined distance.

* * * * *